United States Patent [19]

Voges et al.

[11] 4,048,116
[45] Sept. 13, 1977

[54] CATALYST FOR THE HYDROGENATION OF ACETYLENE ALCOHOLS

[75] Inventors: Dieter Voges, Mannheim; Karl Baer, Weinheim; Juergen Boudier, Duerkheim; Siegfried Winderl, Heidelberg-Wieblingen; Herwig Hoffmann, Frankenthal, all of Germany

[73] Assignee: BASF Aktiengesellschaft, Ludwigshafen, Germany

[21] Appl. No.: 706,471

[22] Filed: July 19, 1976

[30] Foreign Application Priority Data

Aug. 14, 1975 Germany .............................. 2536273

[51] Int. Cl.² ...................... B01J 23/72; B01J 23/84; B01J 23/88

[52] U.S. Cl. ................................. 252/470; 260/635 M
[58] Field of Search .................... 252/470; 260/635 M

[56] References Cited

U.S. PATENT DOCUMENTS 3,479,411  11/1969  Adam et al. ..................... 252/437 X

*Primary Examiner*—W. J. Shine
*Attorney, Agent, or Firm*—Keil, Thompson & Shurtleff

[57] ABSTRACT

An improved catalyst for the complete hydrogenation of acetylenically unsaturated alcohols and based on nickel, copper and manganese. The catalyst is used without a support and molybdenum is additionally included in an amount approximately equal to the content of manganese.

4 Claims, No Drawings

CATALYST FOR THE HYDROGENATION OF ACETYLENE ALCOHOLS

The present invention relates to a hydrogenation catalyst for acetylene alcohols which shows advantages over the prior art catalysts as regards activity, space velocity, life and the yield of saturated mono- and di-alcohols obtainable.

The hydrogenation of acetylene alcohols in contact with nickel or cobalt catalysts has been described, which catalysts have been prepared from alloys of these metals by dissolving out the other components or have been applied to pumice, silica gel, aluminum oxide and other supports (German Pat. Nos. 858,049 and 890,944).

Use was later made of catalysts consisting of from 12 to 20% by weight of nickel, from 1 to 10% by weight of copper and from 1 to 2% by weight of manganese on silicic acid or aluminum oxide (U.S. Pat. Nos. 3,759,845 and 3,449,445) and in some cases on metallic aluminum (German Published Application DOS 2,004,611). The hydrogenation of acetylene alcohols may be carried out in contact with suspended catalysts or fixed catalyst beds.

This hydrogenation is classified into two groups: a single-stage process, i.e. complete hydrogenation in a single pass through the reactor, and a two-stage process. In the latter process, hydrogenation is carried out incompletely in the first stage in contact with, say, a suspended catalyst, that is to say a portion of the alkynol is converted to only the alkenol, hydrogenation being completed in the following reaction zone. The reaction involving the use of the prior art catalysts may be carried out at pressures of from 30 to 400 bars and preferably from 150 to 320 bars. The use of low pressures facilitates the formation of butanol (from butene-diol or the hydroxybutyraldehyde which cannot then be further hydrogenated fast enough), whilst the use of very high pressures, for example pressures above 320 bars, calls for expensive apparatus, a pressure of 320 bars, according to the standards of the chemical industries, being the limit of the particular stage.

In the prior art processes, the hydrogenation temperatures are between 70° C at the inlet and 160° C at the outlet of the reactors.

Initial temperatures below 70° C are not economical when using the prior art catalysts, since unduly long catalyst zones are required to obtain the temperature required to initiate the reaction, whereas tempratures of above 160° C may considerably impair the life of the supported catalysts. It is also known to control the reaction temperatures or the temperature difference between the inlet and outlet of the reactor by recycling.

It is an object of the invention to provide a catalyst for the hydrogenation of acetylene alcohols, particularly 1,4-butynediol, which catalyst permits a much higher throughput as compared with prior art catalysts and also lacks the drawback of the very limited life of supported catalysts whilst showing a high degree of activity with good selectivity, i.e. reduced tendency to form byproducts.

We have found that these and other objects are achieved by a substantially unsupported nickel catalyst which, for example in the form of pellets or tablets, may be preferably used for the hydrogenation of acetylene alcohols to the corresponding saturated alcohols in the liquid phase and in a fixed catalyst bed, which catalyst contains, in addition to nickel as the main ingredient, from about 30 to 40% by weight of copper, based on nickel, and from about 1 to 10% of a mixture of manganese oxide and molybdenum oxide, based on the total weight of the catalyst.

The weight ratio of manganese oxide to molybdenum oxide is generally from 1:10 to 10:1 and preferably about 1:1. The ratio is not critical within the limits given.

A catalyst of this kind may be obtained by precipitating a solution of the metallic compounds, for example the nitrates, with soda solution, filtering the resulting carbonate suspension, washing, calcining, shaping and reducing. Simple compression of a mixture of the particulate oxides, carbonates or hydroxides followed by suitable calcination and reduction also leads to a highly useful catalyst.

At the stage which in many cases is the commercial stage and is that which the catalyst always passes through during manufacture, the catalyst thus usually consists of from about 50 to 80% and preferably from 65 to 70% by weight of nickel oxide, from 15 to 35% and preferably from 23 to 25% by weight of copper oxide, from about 0.3 to 6% and in particular from 3 to 6% by weight of manganese oxide and from 0.1 to 5% and in particular from 1 to 5% by weight of molybdenum oxide, all oxides being calculated as being present in their most stable valency. It is assumed that the subsequent reduction with hydrogen provides the elements other than manganese and molybdenum in the form of metals, the non-reducible elements being present in their lowest stable valency. Compared with the prior art, the invention consists essentially in using 1. a substantially unsupported catalyst and
2. a catalyst which contains molybdenum in addition to the metals nickel, copper and manganese conventionally used in such catalysts.

By these measures the reaction rate and the selectivity of the catalyst, i.e. its ability to cause almost exclusively the hydrogenation of the triple bond to the single bond, are improved in an advantageous manner.

Molybdenum or suitable molybdenum compounds may also be added either before or after decomposition of the carbonates, for example in the form of ammonium molybdate (particularly when added to solutions) or as molybdenum oxide. The pellets or tablets finally obtained are subjected to a tempering process. The pellets or tablets consisting of the oxidic catalyst have a bulk density of from 1.3 to 2 g per cm$^3$ and possess good mechanical strength.

Any acetylene alcohols which may be obtained by the conventional processes are suitable for the hydrogenation. Examples of such acetylene alcohols are dihydric alcohols such as 1,4-butynediol and 2,5-hexynediol, and monohydric alcohols such as 5-dialkylaminopent-3-yne-2-ol and propargyl alcohol. Thus these acetylene alcohols are generally mono- to tri-hydric, mono- or polyacetylenically unsaturated low molecular weight alcohols of, say, from 3 to 15 carbon atoms corresponding to molecular weights of from 56 to about 250. The manufacture of such acetylene alcohols is known. The hydrogenation of the acetylene alcohols is carried out at temperatures of from 40° to 180° C and hydrogen pressures of from about 30 to 320 bars in contact with the catalyst after the latter has been pretreated with hydrogen or reduced.

EXAMPLE 1

Preparation of catalyst

Water is placed in a stirred vessel and a 20% soda solution and an aqueous solution of the nitrates of the metals nickel, copper and manganese are continuously added simultaneously at rates giving a constant pH of 8.5. The nitrate solution contains 9.2% of nickel, 3.2% of copper and 0.8% of manganese, calculated as the element in each case. The resulting mixture of aqueous solution and carbonate suspension passes continuously to a second stirred vessel in which a pH of 6.6 is maintained by the addition of further nitrate solution. Following filtration, washing and drying of the resulting precipitate at 120° C for 12 hours, the resulting solid is calcined at 500° C for a further 12 hours. This mixture of metal oxides is then milled. The resulting powder is divided into four equal portions. The first portion is mixed with nitric acid until it is kneadable, whilst the other portions are mixed not only with nitric acid but also with ammonium molybdate in various amounts to give mixtures containing 1%, 2% and 4% of molybdenum oxide. The mixtures are kneaded, pelleted, and dried for 12 hours at 120° C. The catalyst is ready for use after further calcination at 500° C for 6 hours.

The pellets are then compared with each other in a series of tests. In these tests, 0.5 l of the catalyst to be tested is placed in a pressure-tight reaction tube and is reduced at 260° C at atmospheric pressure under a flow of hydrogen metered in a stream of nitrogen at such a rate that the temperature does not exceed 270° C. Finally, reduction is continued in a stream of hydrogen at 270° C for 12 hours. Following cooling to 30° C, the catalysts are wetted with water and then used for the hydrogenation of a 32% butynediol solution under pressure.

Each catalyst is subjected to two tests under different conditions:

|  | Test 1 | Test 2 |
|---|---|---|
| pressure | 30 bars | 30 bars |
| temperature | 80° C | 120° C |
| offgas | 100 l/hr (STP) | 300 l/hr (STP) |
| feed | 100 ml/hr | 300 ml/hr |

Each test is stopped after 72 hours. The results are listed in the Table below:

TABLE I

| No. | Composition of catalyst (before reduction) | | | | Butanediol in product (% w/w) | |
|---|---|---|---|---|---|---|
|  | NiO | CuO | $Mn_3O_4$ | $MoO_3$ | Test 1 | Test 2 |
| Comparative test | 69.0 | 24.1 | 6.6 | — | 66 | 47 |
| 1 | 68.3 | 23.9 | 6.5 | 1.0 | 67 | 73 |
| 2 | 67.6 | 23.7 | 6.4 | 2.0 | 73 | 78 |
| 3 | 66.2 | 23.3 | 6.2 | 4.0 | 77 | 82 |

EXAMPLE 2

220 l of a catalyst having the composition of Example 1, Test No. 3, were placed in an industrial reactor, reduced and used for the hydrogenation of a 32% aqueous butynediol solution under the conditions given in the Table below. A conventional impregnated catalyst (i.e. a nickel catalyst on a silicate support) had previously been used in the same reactor for said hydrogenation. The carbonyl number of the product discharged from the reactor serves as a quality criterion and should be less than 1.

Whereas the impregnated catalyst had to be replaced on account of strong inactivation after a throughput of 233 parts by weight of butynediol per part by weight of catalyst, the hydrogenation test using the catalyst of the invention was stopped after 76 days (505 parts by weight of butynediol per part by weight of catalyst) with the catalyst still fully active.

The yield of butanediol was from 1 to 1.5% higher from the hydrogenation using the molybdenum-containing unsupported catalyst than when hydrogenation was carried out using the impregnated catalyst.

TABLE II

| Catalyst composition | Impregnated catalyst | Unsupported catalyst |
|---|---|---|
| NiO | 23.0 | 65.6 |
| CuO | 8.0 | 23.0 |
| $Mn_3O_4$ | 2.3 | 4.0 |
| $MoO_3$ | — | 3.8 |
|  | remainder $SiO_3$ | |

| Test conditions | | |
|---|---|---|
| Bulk density (g/l) | 712 | 1,310 |
| porosity ($cm^3$/g) | 0.56 | 0.34 |
| space velocity (kg of butynediol/l of catalyst × hr) | 0.19 | 0.38 |
| liquid throughput ($m^3/m^2$ × hr) | 40 | 40 |
| gas throughput (eff. $m^3/m^2$ × hr) | 31 | 30 |
| temperature at reactor inlet (° C) | 85–100 | 50–80 |
| temperature at reactor outlet (° C) | 150–165 | 110–140 |
| pressure (bars) | 260 | 260 |

EXAMPLE 3

220 l of a catalyst of the composition of Example 1, test no. 2, are placed in the arrangement of Example 2. Following reduction of the catalyst by the method described in Example 1, 90 l/hr of a 60% aqueous solution of hex-3-yne-2,5-diol are passed over the catalyst. At the same time, 800 l of the reactor output are recycled to remove the heat of reaction. Also circulated through the system are about 250 $m^3$/hr of hydrogen (STP) having an inert content of 3%. The pressure in the reactor is 285 bars, the temperature at the reactor inlet is 88° C, and the maximum temperature in the system is 122° C.

The product was shown by gas chromatography to contain from 98.5 to 99.5% by weight of 2,5-hexanediol and from 0.5 to 1% by weight of 2-hexanol.

EXAMPLE 4

1.5 l of a catalyst of the composition of Example 1, test no. 3, are placed in a 2.5-l. reactor for continuous conversion. Following reduction of the catalyst, 500 ml/hr of a mixture of 1 part by weight of fresh 5-diethylaminopent-3-yne-2-ol and 4 parts by weight of the reactor output are passed through the reactor. The temperature at the reactor inlet is 90° C and 110° C at the reactor outlet. The hydrogen pressure is maintained at 300 bars and the off-gas rate is adjusted to 600 l/hr.

The reaction product contains 3.5% of diethylamine, 1.4% of s-butanol, 5.5% of 2-pentanol and 4% of unidentifiable byproducts in addition to 85.6% of 5-diethylaminopentan-2-ol.

We claim:

1. An essentially unsupported nickel catalyst which comprises nickel as the main ingredient, from about 30 to 40% by weight of copper, based on nickel, and from about 1 to 10% by weight of a mixture of manganese and molybdenum oxides, based on the total weight of the catalyst.

2. A catalyst as set forth in claim 1, wherein the ratio of manganese oxide to molybdenum oxide is from 1:10 to 10:1.

3. A catalyst as set forth in claim 1, which is obtained by subjecting a mixture of from about 50 to 80% by weight of nickel oxide, from 15 to 35% by weight of copper oxide, from 0.3 to 6% by weight of manganese oxide and from 0.1 to 5% by weight of molybdenum oxide in a shape suitable for use as a fixed catalyst bed to reduction with hydrogen.

4. A catalyst as set forth in claim 1 wherein said catalyst is in the form of pellets or tablets and wherein said catalyst is designed for the hydrogenation of acetylene alcohols to the corresponding saturated alcohols in liquid phase in a fixed catalyst bed.

* * * * *